(12) United States Patent
Oki et al.

(10) Patent No.: US 9,863,878 B2
(45) Date of Patent: Jan. 9, 2018

(54) PHOTOMETRIC ANALYSIS METHOD AND PHOTOMETRIC ANALYSIS DEVICE USING MICROCHIP, MICROCHIP FOR PHOTOMETRIC ANALYSIS DEVICE, AND PROCESSING DEVICE FOR PHOTOMETRIC ANALYSIS

(71) Applicants: KYUSHU UNIVERSITY, NATIONAL UNIVERSITY CORPORATION, Fukuoka (JP); USHIO DENKI KABUSHIKI KAISHA, Tokyo (JP)

(72) Inventors: Yuji Oki, Fukuoka (JP); Kinichi Morita, Tokyo (JP)

(73) Assignees: USHIO DENKI KABUSHIKI KAISHA, Tokyo (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 232 days.

(21) Appl. No.: 14/769,885

(22) PCT Filed: Feb. 20, 2014

(86) PCT No.: PCT/JP2014/054054
§ 371 (c)(1),
(2) Date: Aug. 24, 2015

(87) PCT Pub. No.: WO2014/132876
PCT Pub. Date: Sep. 4, 2014

(65) Prior Publication Data
US 2016/0011114 A1    Jan. 14, 2016

(30) Foreign Application Priority Data
Feb. 26, 2013   (JP) .................................. 2013-035581

(51) Int. Cl.
*G01N 21/64* (2006.01)
*G01N 21/05* (2006.01)
(Continued)

(52) U.S. Cl.
CPC ...... G01N 21/6428 (2013.01); B01L 3/50273 (2013.01); B01L 3/502715 (2013.01);
(Continued)

(58) Field of Classification Search
CPC ..... B01L 2200/0647; B01L 2300/0654; B01L 2300/0816; B01L 2300/0861;
(Continued)

(56) References Cited

U.S. PATENT DOCUMENTS 6,867,420 B2   3/2005  Mathies et al.
8,354,073 B2   1/2013  Oki et al.
(Continued)

FOREIGN PATENT DOCUMENTS

EP    1843156 A2     10/2007
JP    H07-084220 A    3/1995
(Continued)

OTHER PUBLICATIONS

International Search Report, PCT/JP2014/054054, dated May 13, 2014.
(Continued)

*Primary Examiner* — Maureen Wallenhorst
(74) *Attorney, Agent, or Firm* — Studebaker & Brackett PC

(57) ABSTRACT

In order to carry out various analyses at high accuracy in a site where analysis is needed using a disposable microchip, the microchip is disposed on a display of a tablet terminal device, and a sample or specimen is dropped into a flow path of the microchip to trigger a reaction of the sample in the microchip. Light emitted from the display of the tablet
(Continued)

terminal device is applied to the microchip, and the reaction caused by the applied light in the microchip is measured. When an induced fluorescence method using the applied light is adopted as a measuring method, fluorescence that corresponds to the reaction is observed, and detected by, for example, a built-in camera of the tablet terminal device. The detection signal is analyzed by an arithmetic unit of the tablet terminal device.

33 Claims, 13 Drawing Sheets

(51) Int. Cl.
*G01N 21/03* (2006.01)
*B01L 3/00* (2006.01)
*G01N 33/53* (2006.01)
*G01N 33/536* (2006.01)
*G01N 33/569* (2006.01)

(52) U.S. Cl.
CPC ........ *B01L 3/502753* (2013.01); *G01N 21/03* (2013.01); *G01N 33/5304* (2013.01); *B01L 2200/0647* (2013.01); *B01L 2300/0654* (2013.01); *B01L 2300/0816* (2013.01); *B01L 2300/0861* (2013.01); *B01L 2400/0403* (2013.01); *B01L 2400/046* (2013.01); *B01L 2400/0442* (2013.01); *G01N 21/05* (2013.01); *G01N 33/536* (2013.01); *G01N 33/56966* (2013.01); *G01N 2021/6482* (2013.01); *G01N 2201/0245* (2013.01)

(58) Field of Classification Search
CPC ..... B01L 2400/0403; B01L 2400/0442; B01L 2400/046; B01L 3/502715; B01L 3/50273; B01L 3/502753; G01N 2021/6482; G01N 21/03; G01N 21/05; G01N 21/64; G01N 21/6428; G01N 2201/0245; G01N 33/5304; G01N 33/536; G01N 33/56966

USPC ..... 436/164, 165, 172, 180, 501; 422/82.05, 422/82.08, 69, 551; 435/7.21, 287.2, 435/288.7
See application file for complete search history.

(56) References Cited

U.S. PATENT DOCUMENTS

| 2007/0227967 | A1 | 10/2007 | Sakaino et al. | |
| 2008/0054815 | A1* | 3/2008 | Kotikalapoodi | H05B 33/0815 315/192 |
| 2011/0201382 | A1* | 8/2011 | Hsiao | A61B 5/14532 455/556.1 |
| 2011/0207137 | A1* | 8/2011 | Malik | B01L 7/52 435/6.12 |
| 2012/0244624 | A1* | 9/2012 | Hsiao | G01N 21/8483 436/86 |
| 2014/0036267 | A1* | 2/2014 | Malik | G01N 21/64 356/432 |
| 2015/0244852 | A1* | 8/2015 | Erickson | G06Q 50/22 455/557 |

FOREIGN PATENT DOCUMENTS

| JP | 2005-535871 A | 11/2005 |
| JP | 2007-298502 A | 11/2007 |
| JP | 2009-084128 A | 4/2009 |
| JP | 2009-109232 A | 5/2009 |
| JP | 2012-076016 A | 4/2012 |
| WO | 03/102554 A1 | 12/2003 |
| WO | 2005/119210 A1 | 12/2005 |

OTHER PUBLICATIONS

Nagajima et al, "Developments in Microchip Fluorescence Detecting System Using Organic EL Light Source", College of Industrial Technology, Nihon University, No. 41 (Helsel 20) Scientific Presentation Poster 5, Applied Molecular Chemistry Section Meeting 5-64.

* cited by examiner

TAKING OUT SPECIMEN

DROPPING AND ANALYZING

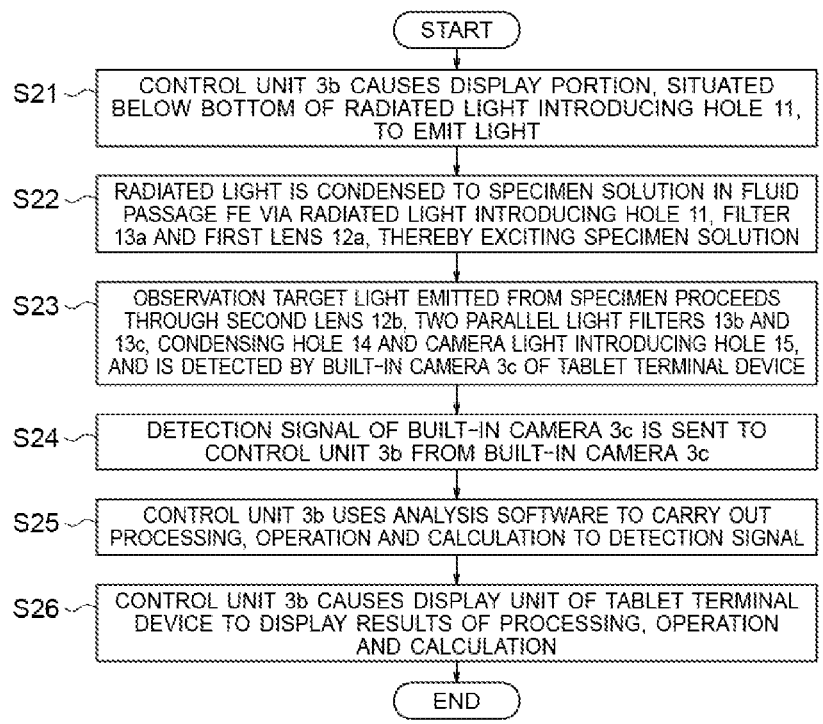
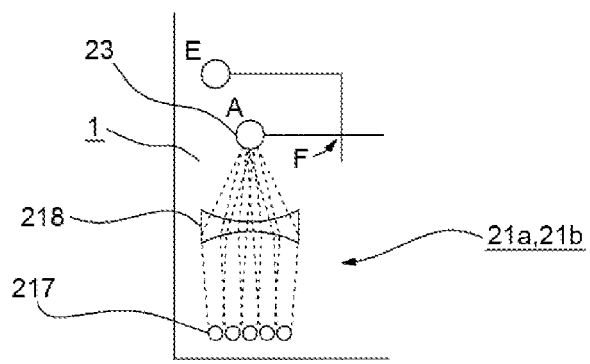

DISPLAYED ANALYSIS
RESULTS AND SO ON

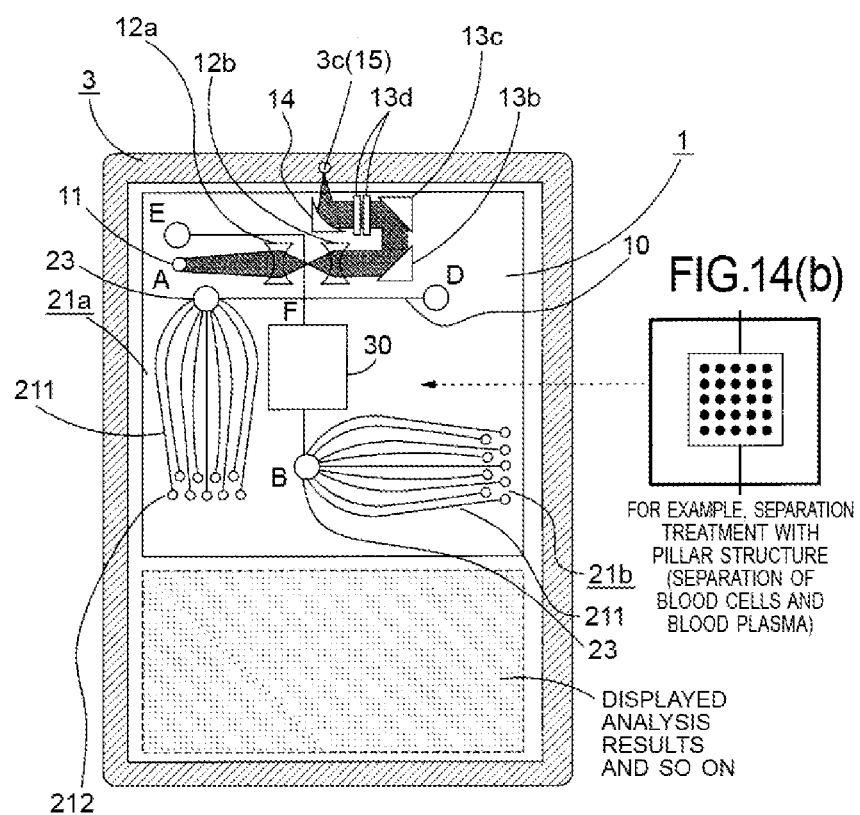

TAKING OUT SPECIMEN

DROPPING

ANALYZING

VARIOUS SETTING, CONTROL DATA LOGGING, DATA TRANSMISSION, AND REPORTING

PHOTOMETRIC ANALYSIS METHOD AND PHOTOMETRIC ANALYSIS DEVICE USING MICROCHIP, MICROCHIP FOR PHOTOMETRIC ANALYSIS DEVICE, AND PROCESSING DEVICE FOR PHOTOMETRIC ANALYSIS

TECHNICAL FIELD

The present invention relates to a photometric analysis method using a microchip that has an analysis channel and other elements provided on a substrate, and a photometric analysis device using such microchip. The present invention also relates to a microchip for the photometric analysis device, and a processing device for the photometric analysis.

BACKGROUND ART

In recent years, a microscale analysis channel or the like is formed on a small substrate made from, for example, silicon, silicone, or glass, by a semiconductor fine processing technology to configure a microchip having the small substrate and the microchannel on the substrate. A microreactor having such microchip and used to isolate, synthesize, extract and analyze a trace amount of sample drug (test drug) is drawing attention.

A reaction analysis system that uses the microreactor is referred to as "micro total analysis system" or "µTAS." When the µTAS is used, a ratio of a surface area of a test drug (sample drug) to a volume becomes large. Thus, a reaction analysis can be carried out at a high speed and high accuracy. It is also possible to make a compact and automated system.

The microchip has a fluid passage (flow path) 10, which is referred to as a microchannel, provided in the microchip. A test drug is disposed in a reaction area of the microchannel. The microchip also has other areas having various functions, in which fluid control elements and components (e.g., micropumps, microvalves, micromixers, filters and sensors) are provided. These areas are integrated in the microchip such that the microchip can be used in various applications.

Typically, the microchip includes a pair of microchip substrates bonded to each other, and a fine channel (microchannel) formed on the surface of at least one of the two microchip substrates. The fine channel is, for example, 10 to several hundred micrometers in width and 10 to several hundred micrometers in depth.

The microchip is typically used in analysis in the fields of chemistry, biochemistry, pharmacology, medical science, and veterinary science, including gene analysis, a clinical diagnosis and a drug screening. The microchip is also often used when synthesizing chemical substances, or measuring environmental data.

For example, when the microchip is used in medicines or medical devices, the microchip is included in (or used as) a preserving container to preserve a living-thing-derived substance (biochemical substance) such as protein, or a analyzing device for such substance. Specifically, the microchip is used in the measurement that takes advantage of intermolecular interaction such as immune reaction in a clinical test or the like (measuring technology using a SPR (surface plasmon resonance), measuring technology using a QCR (quartz crystal microbalance), or measuring technology using a functional surface from a gold colloidal particle to a ultrafine particle.

The microchips can be fabricated at a relatively low cost. Thus, it is possible to prepare and use the microchips in a large quantity depending upon a required quantity in a chemical analysis. Therefore, the microchips can be treated as the disposal devices. It is possible to omit the cleaning and maintenance works after the analysis, unlike ordinary analyzing devices. The cleaning and maintenance works are often troublesome.

Various chemical operations such as mixing of solutions, reactions, isolation, separation, refining and detection can take place in the microchip. When the microchip(s) is incorporated in an analyzing device, the analyzing device detects reactions and other phenomena that take place in the microchip(s). For example, when the microchip is used as an SPR (surface plasmon resonance) sensor, the analyzing device may include a light source having a laser unit (or other light emitting element) to emit monochromatic light, and a light receiving element to receive light from the microchip. The microchip is incorporated in an analyzing device dedicated to a particular use, so as to enable a desired analysis.

On the other hand, many of conventional analyzing devices dedicated to a particular use include large and expensive laser units and/or large and expensive microscopes to carry out desired detection. To deal with such shortcoming, size reduction of the light source and the detecting system, including the detectors, is studied for the analysis-dedicated device.

For example, Patent Literature 1 discloses a detection system that is used with a microchip. The detection system uses a laser diode and an integrated type laser-induced fluorescence detecting element.

Non-Patent Literature 1 discloses the integration of OLED (organic light emitting diodes) into a microchip.

FIG. 15 of the accompanying drawings schematically illustrates an analyzing process that uses a microchip.

Firstly, as shown in FIG. 15(a), a specimen (object to be analyzed) 4 is taken out by a micropipette 2 by a necessary amount for analysis. The specimen 4 is obtained from, for example, a human body, an animal, river or wasted liquid. A pretreatment may be conducted before the specimen 4 is taken out by the micropipette 2 to remove impurities or the like, if necessary. Then, the specimen 4 is dropped into a fluid passage (flow path) of a microchip 1 from the micropipette 2 (FIG. 15(b)).

The specimen is received in the microchip 1 and a reaction of the specimen takes place (e.g., a biomolecular reaction between an antigen and an antibody) in the microchip 1. Subsequently, the microchip 1 is loaded in an analyzing device 5. The reaction of the specimen is detected by the analyzing device 5 with light emitted from a light source of the analyzing device 5. The detection results, in the form of detection signals, are processed by a control tool 5a. The control tool 5a processes and analyzes the detection signals. The control tool 5a is also used to display the analysis results, control various setting of the analyzing device 5, log-in data, and send data (FIG. 15(c)). The analysis-dedicated device includes the analyzing device 5 and the control device 5a.

LISTING OF REFERENCES

Patent Literatures

PATENT LITERATURE 1: Japanese Patent Application Laid-Open Publication No. 2005-535871
PATENT LITERATURE 2: Japanese Patent Application Laid-Open Publication No. 7-84220

PATENT LITERATURE 3: Japanese Patent Application Laid-Open Publication No. 2009-84128
PATENT LITERATURE 4: Japanese Patent Application Laid-Open Publication No. 2007-298502
PATENT LITERATURE 5: Japanese Patent Application Laid-Open Publication No. 2009-109232
PATENT LITERATURE 6: Japanese Patent Application Laid-Open Publication No. 2012-76016

Non-Patent Literature(s)

NON-PATENT LITERATURE 1: College of Industrial Technology, Nihon University, No. 41 (Heisei 20) Scientific Presentation Poster 5, Applied Molecular Chemistry Section Meeting 5-64, "Developments in Microchip Fluorescence Detecting System Using Organic EL Light Source," Hizuru Nagajima, et al. URL (searched Dec. 20, 2012): http://itc.cit.nihon-u.ac.jp/enkyu/kouennkai/reference/No.41/5_ouka/5-064.pdf>

SUMMARY OF THE INVENTION

Problems to be Solved by the Invention

In the life science technology of recent years, there is an increasing demand for POCT (point of care testing). In other words, there is an increasing demand for a compact and portable measuring device that performs the testing in a short time and provides evaluation and analysis at a high accuracy at a working site where the analysis is necessary.

Although the microchip itself is small (compact) and portable, the measuring device is not always small and portable. As described above, the conventional analysis-dedicated device has a large laser (large light source for detection) unit and a large microscope. Usually the conventional analysis-dedicated device is installed in a research institute, and not portable.

The detecting system disclosed in Patent Literature 1, which uses a laser diode and an active element (or elements) of an integrated type laser-induced fluorescence detecting element, is compact and portable, but it is configured and designed for a particular analysis. In order to cope with a variety of analyses, therefore, a large number of detecting systems should be prepared. The laser-induced fluorescence detecting element has an amorphous silicon photodiode, and an optical interference filter integrated and patterned on the amorphous silicon photodiode. The optical interference filter is thick and made from $SiO_2/Ta_2O_5$. The laser-induced fluorescence detecting element, therefore, has a complicated structure and is expensive.

When the OLEDs (organic light emitting diodes) are integrated in a microchip as disclosed in the Non-Patent Literature 1, the microchip may be integrated with the detection system, and the characteristics of the microchip (i.e., being compact and portable) are maintained. However, because the active element is included, the microchip becomes expensive. In addition, because a battery is integrated to the microchip to feed an energy to the active element, it is difficult to use the microchip as a disposal device when the cost is considered.

The present invention was developed in view of the above-described situation, and an object of the present invention is to provide an optical analyzing method and an optical analyzing device that can deal with various analyses, use a disposal microchip and carry out evaluations and analyses at a site where the analyses are needed in a short time at high accuracy. Another object of the present invention is to provide a microchip and a processing device for the optical analysis, which are suitable for such optical analyses.

Solution to the Problems

The present invention uses a processing device that includes a display unit (display portion) for displaying an image, and a control unit for controlling an image to be displayed on the display unit and for performing operation and calculation (arithmetic processing). A microchip is disposed on the display unit of the processing device, and light is introduced to the microchip from the display unit for the optical analysis.

The processing device may include a tablet computer (tablet terminal device), a smartphone, a portable telephone, a personal computer, or other processing devices. In the following description, the tablet terminal device will be described as an example. The display unit may include a liquid crystal display device or an organic EL (electroluminescent) display device.

In the present invention, as shown in FIG. 1, a microchip 1 is placed on a display unit 3a of a processing device, such as the above-described tablet terminal device 3. It should be noted that the microchip 1 may be placed on the display unit 3a, or may be supported above the surface of the display unit 3a at a predetermined small distance (gap).

FIG. 2 shows a schematic process for exemplary analysis according to the present invention.

Firstly, as shown in FIG. 2(a), the specimen (object to be analyzed) 4 is taken out by a micropipette 2. The specimen is taken out by an amount necessary for analysis. The specimen 4 is obtained from, for example, a human body, an animal, river or wasted liquid. It should be noted that a pretreatment may be conducted before the specimen is taken out by the micropipette 2 to remove impurities or the like, if necessary.

The specimen 4 is dropped from the micropipette 2 to a fluid passage of the microchip 1 on the display unit 3a of the tablet terminal device 3 (processing device).

As a result, a reaction of the specimen 4 (e.g., a biomolecular reaction between an antigen and an antibody) takes place in the fluid passage of the microchip 1.

The microchip 1 is irradiated with light emitted from the display unit 3a of the tablet computer 3. It should be noted that the radiated light may be used after the wavelength of the radiated light is selected. The wavelength selection may be made by switching three primary colors of a display mechanism, or embedding an appropriate (or necessary) wavelength filter in a light introducing portion of the microchip 1.

As the microchip is irradiated with the light, the reaction that takes place in the microchip 1 is measured. For example, when a light-induced fluorescence method is employed as a measuring method that uses the irradiation of light, fluorescence that corresponds to the reaction is observed.

The microchip 1 has a light introducing (inlet) portion and a light exit (outlet) portion, and receives light that comes from the display unit 3a of the tablet terminal device 3, at the light introducing portion. Light received by the microchip 1 is directed to the fluid, which contains the specimen 4 introduced into the microchip 1, and causes the specimen-containing fluid to emit light. The light emitted from the specimen-containing fluid is guided to the outside from the light exit portion.

It should be noted that the microchip may include a light bring-in unit (collecting unit). The light bring-in unit may have a light bring-in portion (collecting portion) for collecting light, which is introduced from the light introducing portion, and a light guiding unit for guiding the light, which is brought-in (collected) by the light bring-in portion, to the light irradiation position on the microchip. The light collected by the light bring-in unit may control the flow of the fluid, which contains the specimen introduced into (to) the microchip.

The light emitted from the specimen upon reaction in the microchip 1 is recognized by visual inspection (observation by human eyes), i.e., light emission (or no light emission) is confirmed by visual inspection. Thus, presence (or absence) of the reaction in the microchip 1 is determined.

On the other hand, when a light receiving element (e.g., a camera) is built in the tablet computer 3, the light emitted from the specimen upon the reaction in the microchip 1 is guided to the light receiving element. Then, the reaction is detected by the light receiving element of the tablet computer 3.

Automatic positioning or the like may be carried out if a resolving power of the camera is utilized. A dispersing element may be provided in the microchip 1 in order to measure a spectrum of a signal light. A detection signal generated from the light receiving element is operated and calculated (arithmetically processed) by an operating and calculating unit (arithmetic unit) of the tablet computer 3. The operating and calculating unit processes and analyzes the detection signal, and also displays the analysis result on the display unit 3a (FIG. 2(b)). The operating and calculating unit also performs the logging in of the data, and the transmission of the data.

A set of software used to analyze (process, operate and calculate) the detection signal may be downloaded from outside depending upon analysis contents to be applied to the specimen. The downloading may be performed by using a communication function of the tablet computer 3. Appropriate software may be selected from the set of downloaded software when the measurement and analysis are conducted, depending upon analysis items to be applied to the measurement target. The downloaded set of programs (software) for analysis may be updated to a new version of programs at an appropriate timing by using the communication function of the tablet computer 3.

Specifically, the present invention solves the above-described problems in the following manner.

(1) An optical analyzing method analyzes a specimen introduced into a microchip having a light inlet and a light outlet. The method includes preparing a processing device that includes a display unit (display portion) for displaying an image, and a built-in control unit for carrying out operation and calculation (arithmetic processing) and controlling the image to be displayed on the display unit. The method also includes placing the light inlet of the microchip on the display unit (display portion) of the processing device. The method also includes causing that part of the display unit which corresponds to the light inlet to emit light, introducing the light into the microchip, irradiating a fluid, which contains the specimen introduced into the microchip 1, with the emitted light, causing the fluid, which contains the specimen, to emit second light, and analyzing the specimen with the second light.

(2) An optical analyzing device includes a processing device and a microchip. The processing device has a display unit (display portion) for displaying an image, and a built-in control unit for carrying out operation and calculation (arithmetic processing) and controlling the image to be displayed on the display unit. The microchip has a light inlet and a light outlet. The light inlet of the microchip is placed on a predetermined position of the display unit. The control unit of the processing device is configured to cause that part of the display unit which corresponds to the light inlet to emit light, introduce the light into the light inlet from the display unit, irradiate a fluid, which contains the specimen introduced into the microchip, with the light, cause the fluid, which contains the specimen, to emit second light, and cause the second light to exit from the light outlet.

(3) In the optical analyzing device of (2), the microchip may include a light bring-in unit (collecting unit). The light bring-in unit may have a light bring-in portion (collecting portion) for collecting the light introduced from the light inlet, and a light guiding unit for guiding the light, which is collected by the bring-in portion, to a light irradiation position of the microchip.

(4) In the optical analyzing device of (2) or (3), the processing device may include an image receiving unit. The light outlet of the microchip may be placed at a position that allows the image receiving unit to receive the light exiting from the light outlet. The control unit may carry out the operation and calculation (arithmetic processing) based on an optical signal representing the light, which exits from the light outlet and is received by the image receiving unit, to analyze the specimen.

(5) In the optical analyzing device of (2) or (3), the light outlet of the microchip may be placed at a position that allows the light, which exits from the light outlet, to be observed by a human eye or human eyes.

(6) In the optical analyzing device of (2), (3), (4) or (5), the microchip may be configured to take a wavelength component that is necessary to excitation of the specimen from the light introduced from the light inlet to obtain radiation light. The microchip may also be configured to irradiate the fluid, which contains the specimen introduced into the microchip, with the radiation light to cause the fluid, which contains the specimen, to emit the second light. The microchip may include a passive element configured to cut off the radiation light component from the second light emitted from the fluid, which contains the specimen, such that light from the passive element is guided to the light outlet.

(7) In the optical analyzing device of (2), (3), (4), (5) or (6), the microchip may include a pretreatment filter configured to separate (isolate) a substance, which is not the specimen, from the fluid, which contains the specimen, before the fluid, which contains the specimen, is irradiated with the light.

(8) A microchip is configured to be placed on a display unit of a processing device, and optically analyze a specimen introduced into the microchip upon light emission of the display unit. The processing device has the display unit for displaying an image. The microchip includes a light inlet and a light outlet. The light inlet is configured to receive light upon light emission of the display unit of the processing device. The microchip is configured to irradiate a fluid, which contains the specimen introduced into the microchip, with the received light, and to cause the fluid, which contains the specimen, to emit second light. The light outlet is configured to guide the second light emitted from the fluid, which contains the specimen, to outside.

(9) A processing device for optical analysis includes a display unit configured to display an image, and a built-in control unit configured to carry out operation and calculation and to control the image to be displayed on the display unit.

The processing device is configured to introduce light to a microchip from the display unit to analyze a specimen introduced into a microchip. The microchip has a light inlet and a light outlet, and is placed on the display unit. The control unit of the processing device is configured to cause that part of the display unit which corresponds to the light inlet to emit light, to guide the light emitted from the display unit to the light inlet, to irradiate a fluid, which contains the specimen introduced into the microchip, with the light, and to carry out the analysis with the microchip.

Advantageous Effects of the Invention

The present invention has the following advantages.

(1) In the present invention, the optical analyzing method uses the processing device that has the display unit for displaying an image, and the built-in control unit for carrying out the operation and calculation and for controlling the image to be displayed on the display unit. A microreactor (i.e., the microchip) is placed on the display unit. Thus, it is possible to separate, isolate, synthesize, extract and analyze a trace amount of sample (reagent). The light from the display unit can be used as the detection light for an analysis target and/or the energy source for driving. The operating and calculating unit, which is built in the processing device, can be used to operate, calculate and analyze the detection data obtained from the analysis target. It is also possible to display the analysis results on the display unit.

In the present invention, therefore, the light source for detection and the operating and calculating unit are integrated in a single processing device having the display unit. If a portable device is used as the processing device, it is possible to carry out evaluation and analysis at a site where analysis is needed, in a short examination time at high precision. In other words, the present invention can meet a demand for point of care testing (POCT) in the life science field.

(2) Because the light emitted from the display unit can be used as the detection light for the analysis target and the energy for driving, the microchip can have no active element and can be a conventional inexpensive microchip. Such microchip can be treated as a disposal element. For example, it is not necessary to use an expensive microchip that is integrated with a detection system having, for example, integrated organic EL (electroluminescence) elements and other elements.

The light source and the energy source are derived from the display unit of the processing device. Thus, even if the position of the microchip on the display unit changes to a certain extent, the analyzing device can automatically adjust the light emitting position in accordance with the changed position. Accordingly, the position adjustment of the microchip on the tablet terminal device is not necessary, and the measurement can be performed quickly.

(3) If the processing device has a communication function (communication unit), the processing device may use the communication unit to download the software for the analysis, depending upon the details of the analysis to be performed on the measurement target. Thus, the analyzing device of the invention can be employed as an analyzing device that can cope with a variety of analyses for a variety of specimens.

Therefore, unlike the conventional configuration that uses a dedicated detection system designed for a particular analysis, the present invention can deal with various analyses, and it is not necessary to prepare many analyzing devices customized for the respective analyses.

(4) According to the present invention, the logging of the measurement data to the processing device is easy, and therefore a dedicated storage unit is not necessary. Also, the analyzing system using a communication function can be established easily. Furthermore, it is possible to customize the displaying manner of the display unit depending upon the selection of emitted light color and the indication (displaying) of the analysis data.

BRIEF DESCRIPTION OF THE DRAWINGS

FIG. 2(a) shows a specimen (object to be analyzed) taken out by a micropipette, and FIG. 2(b) shows a tablet computer and a microchip into which the specimen is dropped for analysis.

FIG. 8 shows a flowchart of an analysis procedure performed by a tablet device (processing device).

FIG. 9 shows another exemplary configuration of the light collecting unit.

FIG. 10(a) shows a cross-sectional view of a collimator lens array and optical path changing holes in the microchip disposed on the display unit, and FIG. 10(b) shows a cross-sectional view taken along the line P-P in FIG. 10(a).

FIG. 14(a) shows the microchip of the first embodiment together with a pretreatment filter, which is incorporated in the microchip, and FIG. 14(b) shows the pretreatment filter having a pillar structure.

FIG. 15(a) shows a specimen taken out by a micropipette, FIG. 15(b) shows the micropipette and a microchip, and FIG. 15(c) shows an analyzing device.

DETAILED DESCRIPTION OF THE INVENTION

Embodiments of the present invention will be described in detail below. It should be noted that the present invention is not limited to the illustrated embodiments. Various changes and modifications may be made to the embodiments within the object of the present invention. In the following description, redundant description may be omitted, but this does not intend to limit the scope of the invention.

First Embodiment

Figure 1:
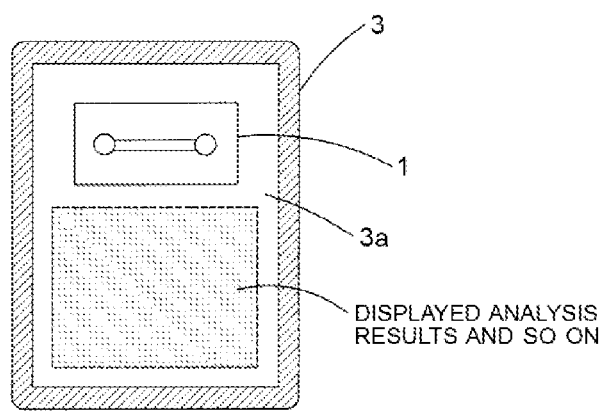
FIG. 1 shows a schematic view of an analysis device according to one embodiment of the present invention.
Figure 2A:
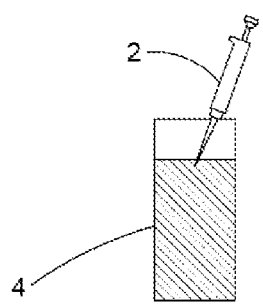
FIG. 2(a) and FIG. 2(b) show in combination a schematic process for exemplary analysis according to the present invention. Specifically.
Figure 2B:
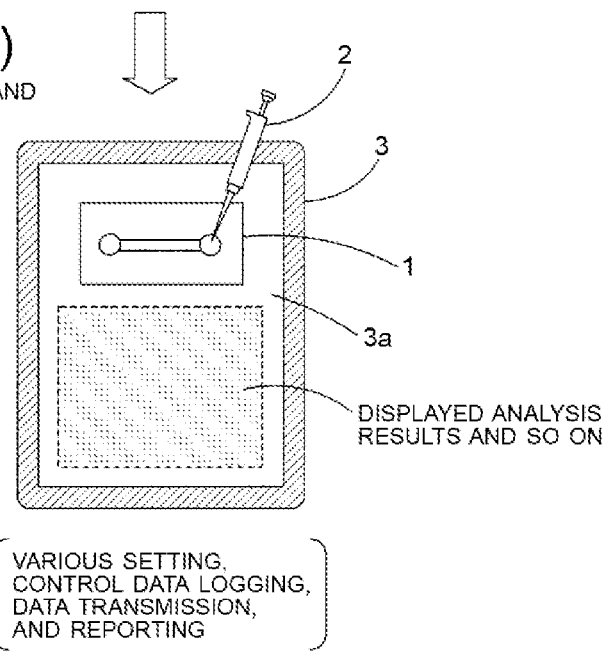
Figure 3:
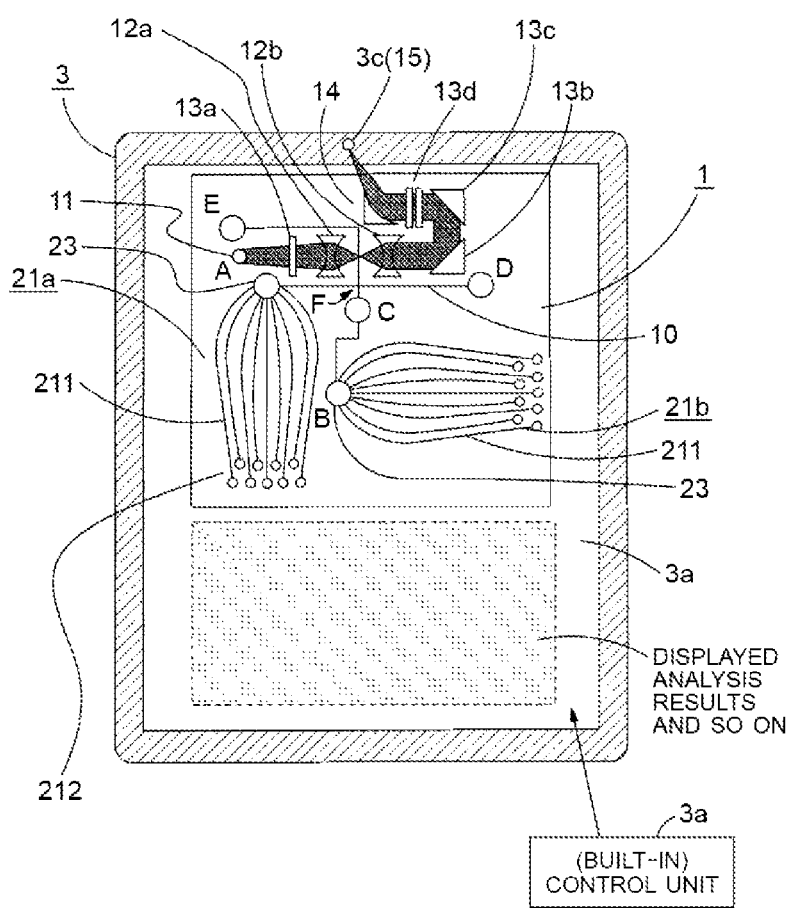
FIG. 3 shows a first embodiment of the present invention.

FIG. 3 shows a first embodiment of the present invention. In this embodiment, a portable tablet device 3 is used as the above-described processing device that includes the display unit (display portion) and the built-in control unit. The tablet device 3 has a built-in camera as a light receiving element. The microchip 1 is placed on the surface of the tablet device 3 in an area including part of the display unit 3a and the built-in camera 3c. It should be noted that the microchip 1 may be supported above the above-mentioned area at a predetermined small distance (e.g., about 1 mm).

It should also be noted that for the sake of easier understanding the size of the microchip 1 is exaggerated in the drawing. Thus, the real size relationship between the tablet terminal device 3 and the microchip 1 may be different from what is depicted in FIG. 3.

The microchip 1 is made from, for example, silicone resin such as PDMS (Polydimethylsiloxane). As shown in FIG. 3, the microchip 1 has, at least, a light inlet or introducing portion (e.g., hole 11 for introducing radiated light, and light inlets of light collecting units 21a and 21b), a light outlet or exit portion (e.g., hole 15 for introducing light to the built-in camera), a plurality of ports (ports A-E) for retaining the specimen-containing liquid, and/or buffer solution, a fluid passage (micro fluid passage 10) connecting the ports A-E, light-driven liquid conveying units (e.g., light-driven air pump 23) provided at the ports for conveying (transporting) the liquid, which is retained in the associated ports, the light collecting units (light collecting units 21a and 21b) for collecting (bringing in) the light emitted from the display unit and introduced from the light introducing portion and for guiding the light to the liquid conveying units and the like, a light guiding path (path defined by the filter 13a, the first lens 12a and other components) for guiding the light from the light introducing portion and irradiating the specimen-containing liquid with the light, and another light guiding path (path defined by the second lens 12b, the first parallel light filter 13b, the second parallel light filter 13c and other components) for guiding light, which is emitted from the specimen upon irradiating the specimen-containing liquid with the light, to the light exit portion.

Each of the light collecting units may include, for example, a liquid crystal optical collimator microlens array and optical fibers, which is disclosed in Patent Literature 2.

Figure 4:
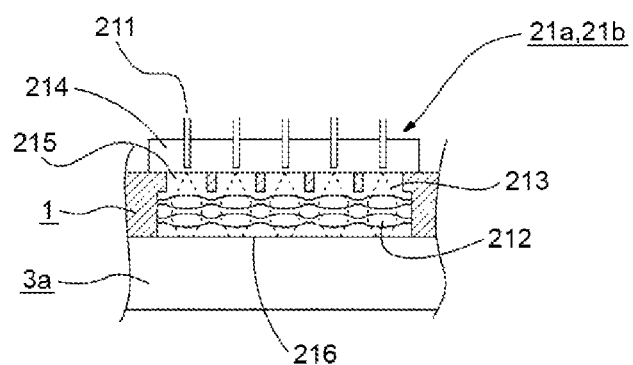
FIG. 4 shows a detailed view of a light collecting portion of a light collecting unit.

FIG. 4 shows the detail of the light collecting portion of each of the light collecting units 21a and 21b. The microchip 1 has a liquid crystal optical collimator microlens array 212 (hereinafter, occasionally referred to as "collimator lens array") for collimating the light emitted from the display unit 3a (e.g., liquid crystal panel), and a liquid crystal light-collecting microlens array 213 (hereinafter, occasionally referred to as "light-collecting lens array) for collecting the light emitted from the collimator lens array 212 to the front ends of the optical fibers 211. The collimator lens array 212 is disposed to face the display unit 3a, and the light-collecting lens array 213 is disposed to face the optical fibers 211. Light-collecting holes 215 are formed in the light exit face of the light-collecting lens array 213.

In each of the light-collecting holes 215, which are formed to match the number of the microlenses, received is the front end of the corresponding optical fiber 211 to receive the light (collected light) emitted from the light-collecting lens array 213. The optical fibers 211, which correspond to the light-collecting holes 215 respectively, are positioned by an optical fiber manifold 214. On the other hand, the light exits of the optical fibers 211 are inserted in, for example, the port A of the microchip 1 and secured by a manifold (not shown).

The light emitted from the display unit 3a is incident to the microlenses of the collimator lens array 212. The incident light is collimated by the respective microlenses of the collimator lens array 212, and guided to the microlenses of the light-collecting lens array 213, which are situated above the microlenses of the collimator lens array, respectively. The collected light, which exits from the respective microlenses, proceeds through the light collecting (condensing) holes 215 and is incident to the front ends (inlets) of the optical fibers 211 attached to the light condensing holes 215. The light incident to the respective optical fibers 211 is emitted from the outlets of the respective optical fibers 211, which are inserted in, for example, the port A of the microchip 1.

Two sets of light collecting units are provided in this embodiment. One set (light collecting unit 21a) guides the light, which is emitted from the display unit 3a, to the port A of the microchip 1, as described above. The other set (light collecting unit 21b) guides the light, which is emitted from the display unit 3a, to the port B of the microchip 1.

Referring back to FIG. 3, the light-driven air pumps 23 and 23 (light-driven micropumps) are provided in the ports A and B, respectively. The light-driven air pumps 23 and 23 may be those which are disclosed in Patent Literature 3. For example, the light-driven air pump 23 has a gas generating chamber to retain a gas generating agent which generates a gas when it is irradiated with light. The gas generated upon irradiation causes the fluid to move in the fluid passage 10.

The light-driven air pump 23 is driven upon introducing the light to the port B from the display unit 3a.

The functions and roles of the respective ports shown in FIG. 3 are described below.

The port A is a reservoir of solution. The light-driven air pump 23 is provided at the port A. The specimen is introduced to the port A.

The port B is a port at which another light-driven air pump 23 is provided.

The port C is a reservoir of solution to receive and reserve, for example, a buffer solution (PBS or phosphate buffered saline).

The port D is a reservoir of the specimen.

The port E is an exit of the specimen.

In this embodiment, the analysis on the specimen introduced into the microchip will generally be carried out in the following manner.

The light introducing portions (radiated light inlet 11, and the light inlets of the light collecting units 21a and 21b) of the microchip are placed on the display unit 3a of the tablet device 3. Those areas (positions) on the display unit which correspond to the light introducing portions are caused to emit light such that the light is introduced into the microchip 1. This light drives the liquid conveying unit (e.g., light-driven air pump(s) 23), and controls the flow of the fluid, which contains the specimen introduced into the microchip 1. Also, the fluid, which contains the specimen, is irradiated with the light such that the fluid, which contains the specimen, emits another light (second light). The analysis of the specimen is carried out with the second light.

Figure 5:
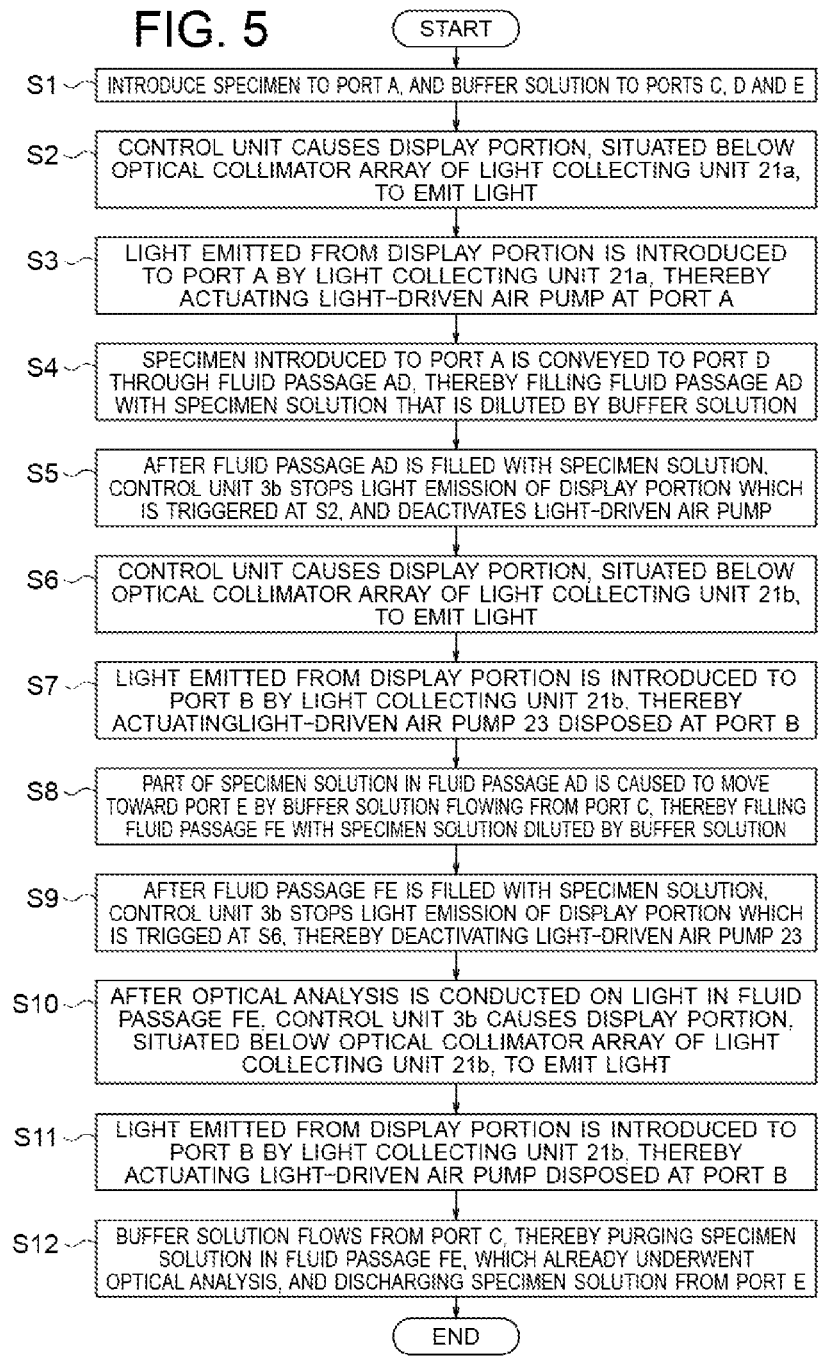
FIG. 5 is a flowchart of an analysis method of the embodiment of the present invention.

Referring now to FIG. 5, the analyzing process of this embodiment will be described. In this embodiment, the specimen introduced into the microchip 1 moves in the fluid passage 10 in the microchip 1 and undergoes the analyzing process in the manner shown in FIG. 5.

Firstly, the specimen is introduced from the port A. The buffer solution (e.g., PBS) is introduced from the ports C, D and E (Step S1).

Then, the control unit 3b which is built in the tablet terminal device 3 causes that part of the display unit, which is located below the liquid crystal collimator microlens array 212 (optical collimator array) of the light collecting 21a, to emit light (Step S2).

The light emitted from the display unit 3a is introduced to the port A by the light collecting unit 21a, and the light-driven air pump 23 disposed at the port A is driven (Step S3).

As the light-driven air pump 23 is driven, the specimen introduced into the port A at Step S1 is caused to move in the fluid passage AD (fluid passage 10 between the ports A and D) toward the port D. In the fluid passage AD, the specimen introduced into the port A meets the buffer solution (PBS) introduced to the port D such that the fluid passage AD is filled with the solution of the specimen that is diluted by the buffer solution (PBS) (Step S4).

It should be noted that the buffer solution may be introduced to the port A and the specimen may be introduced to (into) the port D in Step S1. In Step S4, the light-driven air pump 23 may be driven such that the buffer solution may be conveyed from the port A toward the specimen at the port D.

After the fluid passage AD is filled with the solution of the specimen that is diluted by the buffer solution (PBS) at Step S4, the control unit 3b of the tablet terminal device 3 stops the light emission of that part of the display unit 3a which is situated below the light collimator array 212 of the light collecting unit 21a, and deactivates the light-driven air pump 23 (Step S5).

Subsequently, the control unit 3b of the tablet terminal device 3 causes that part of the display unit 3a which is situated below the liquid crystal collimator lens array 212 (light collimator array) of the light collecting unit 21b to emit light (Step S6). The light emitted from that part of the display unit 3a is introduced to the port B by the light collecting unit 21b, and the light-driven air pump 23 disposed at the port B is driven (Step S7).

As the light-driven air pump 23 is driven, the gas generated at the port B and the buffer solution introduced to the port C at Step S1 are caused to move in the fluid passage CE (fluid passage 10 between the ports C and E) toward the port E. Therefore, the solution of the specimen, which is diluted by the buffer solution (PBS) and present at the intersection F of the fluid passages CE and AD, is caused to move toward the port E from the intersection F by the buffer solution flowing from the port C. Accordingly, part of the solution of the specimen diluted by the buffer solution (PBS) in the fluid passage AD is caused to move toward the port E together with the buffer solution flowing from the port C. In other words, the buffer solution flowing from the port C forces that part of the solution of the specimen to move toward the port E. This part of the solution of the specimen meets the buffer solution (PBS) introduced to the port E in the fluid passage FE (fluid passage 10 between the intersection F and the port E) such that the fluid passage FE is filled with the solution of the specimen diluted by the buffer solution (PBS) (Step S8).

After the fluid passage FE is filled with the solution of the specimen diluted by the buffer solution (PBS) at Step S8, the control unit 3b of the tablet terminal device 3 stops the light emission of that part of the display unit 3a which is situated below the light collimator array of the light collecting unit 21b, and deactivates the light-driven air pump 23 (Step S9).

The optical analyzing unit (will be described) conducts the optical analysis on the light in the fluid passage FE. Then, the control unit 3b of the tablet terminal device 3 causes that part of the display unit 3a, which is located below the light collimator array of the light collecting unit 21b, to emit light (Step S10). The light emitted from that part of the display unit 3a is introduced to the port B by the light bring-in unit 21b, and the light-driven air pump 23 disposed at the port B is driven (Step S11). As the light-driven air pump 23 is driven, the buffer solution is caused to move from the port C, as described above. Thus, the solution of the specimen in the fluid passage FE, which is diluted by the buffer solution (PBS) and already underwent the optical analysis, is purged by the buffer solution (more precisely, a flesh solution of the specimen, which is diluted by the buffer solution (PBS) and does not yet undergo the optical analysis, and which contains the solution of the specimen derived from the intersection F) such that the solution of the specimen is discharged from the port E (Step S12).

As shown in FIG. 3, the optical analyzing unit used to carry out the optical analysis on the light in the fluid passage FE includes, for example, the radiated light introducing hole 11, a filter 13a, the first lens 12a, a second lens 12b, two parallel light filters (first parallel light filter 13b and second parallel light filter 13c), a filter 13d, a light condensing hole 14 and a light introducing hole 15 for the built-in camera.

Figure 6:
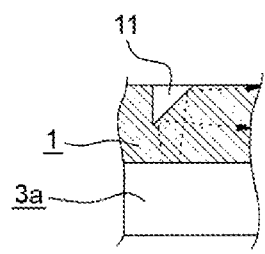
FIG. 6 shows a cross-sectional view of a radiated light inlet hole.

FIG. 6 shows the cross-sectional view of the emitted light introducing hole 11. The bottom of the light introducing hole 11 has an inclined wall, which is inclined relative to the surface of the microchip 1.

The light emitted from that part of the display unit 3a of the tablet terminal device 3, which is situated below the bottom of the light introducing hole 11, is incident to the bottom of the light introducing hole 11. The microchip 1 is made from silicone resin such as PDMS, as described above. In general, the refractive index of the silicone resin is greater than the refractive index of the air (atmosphere). Thus, when the light emitted from the display unit is incident to the inclined bottom wall of the light introducing hole 11 at an incident angle that is equal to or greater than a critical angle of the microchip 1 (silicone resin) to the air, then the light is totally reflected by the bottom wall. By appropriately deciding the angle of the inclined wall, the light emitted upward from the display unit 3a is reflected (turned) to a transverse direction (lateral direction) by the inclined wall of the light introducing hole.

The emitted light from the display unit is diffused light, and therefore a certain component of the light proceeding in the transverse direction spreads in the vertical direction, and is incident to the upper surface of the microchip 1. The light incident to the upper surface of the microchip 1 is reflected at the interface between the microchip 1 and the air and guided toward the first lens 12a if the incident angle is equal to or greater than the critical angle of the microchip 1 (silicone resin) to the air.

Thus, the optical path in the microchip 1 (silicone resin) through which the light proceeds from the light introducing hole 11 to the first lens 12a) serves as the waveguide (light guiding path) for the emitted light.

It should be noted that the filter 13a is disposed in the optical path between the light introducing hole 11 and the first lens 12a. The emitted light from the display unit 3a is directed to the specimen in the fluid passage FE, i.e., the light is used as the light to excite the specimen in the fluid passage FE.

The control unit 3b, which is built in the tablet terminal device 3, causes that part of the display unit 3a, which is located below the light introducing hole 11, to emit light such that the light has a wavelength suitable for excitation of the specimen. The light emitted from the display unit 3a has a relatively wide spectral line width. Accordingly, the light emitted from the display unit 3a may contain a wavelength component that is not necessary for the excitation of the specimen. The unnecessary wavelength component in the light may become a cause of error in the measurement. The filter 13a removes (cuts off) such unnecessary wavelength component from the light emitted from the display unit.

The first lens 12a is defined by a hollow space formed in the microchip 1. The light incident surface of the first lens 12a, to which the light emitted from the display unit is incident, is concave, and the exiting surface of the first lens is also concave. The concave shape of the light incident surface and the concave shape of the light exiting surface are decided such that the light passing through the first lens 12a is incident to the fluid passage FE of the microchip 1 and condensed in the fluid passage FE.

Thus, the hole 11 for introducing the emitted light collects the light emitted from the display unit 3a and reflects the light toward the filter 13a and the first lens 12a. The reflected light proceeds in the microchip 1, which is made from the silicone resin for example, and is incident to the filter 13a and the first lens 12a. The light emitted from the display unit 3a and incident to the first lens 12a via the filter 13a is condensed in the fluid passage FE by the first lens 12a, and the solution of the specimen diluted by the buffer solution (PBS) in the fluid passage FE is excited by the light.

As the specimen is excited by the light, the specimen emits light (e.g., fluorescence) depending upon the physical property of the specimen. This light proceeds through the second lens 12b, two parallel light filters (first parallel light filter 13b and second parallel light filter 13c), a filter 13d, a condensing hole 14 and the light introducing hole 15 for the built-in camera in this order, and is incident to the built-in camera 3c of the tablet terminal device 3 such that the light is detected by the built-in camera 3c. This light is light to be observed (observation target light).

The second lens 12b is defined by a hollow space formed in the microchip 1. The incident surface of the second lens 12b, to which the observation target light is incident, and the exit surface of the second lens have curved shapes such that the exiting light from the second lens 12b becomes parallel light.

The first parallel light filter 13b is defined by a hollow space formed in the microchip 1. The hollow space has a shape of, for example, a triangular prism. The parallel light that exits from the second lens 12b is incident to the inclined surface of the triangular filter 13b. The inclined surface of the triangular filter 13b is inclined 45 degrees relative to the optical axis of the parallel light. When the material of the microchip 1 is PDMS that has a refractive index of 1.41, then the critical angle of the PDMS is approximately 45 degrees. Thus, the incident angle of the parallel light to the inclined surface of the triangular filter 13b is almost equal to the critical angle, and the parallel light incident to the inclined surface of the filter 13b is totally reflected at right angles (upward in FIG. 3).

The second parallel light filter 13c is defined by a hollow space formed in the microchip 1. The hollow space has a shape of, for example, a triangular prism. The parallel light from the first parallel filter 13b is incident to the inclined surface of the triangular filter 13c. The inclined surface of the triangular filter 13c is inclined 45 degrees relative to the optical axis of the parallel light. Similar to the first parallel light filter 13b, the incident angle of the parallel light to the inclined surface of the second parallel light filter 13c is almost equal to the critical angle, and the parallel light incident to the inclined surface of the filter 13c is totally reflected at right angles (leftward in FIG. 3).

As described above, when the material of the microchip 1 is the PDMS, the critical angle of each of the first parallel light filter 13b and second parallel light filter 13c is approximately 45 degrees. Thus, each of the first and second parallel light filters 13b and 13c totally reflects that component of the incident light which has an incident angle equal to or greater than 45 degrees.

The light incident plane of each of the first and second parallel light filters 13b and 13c is inclined 45 degrees relative to the optical axis of the incident parallel light. Thus, when the light is incident to the first parallel light filter 13b at the incident angle greater than 45 degrees, the light is totally reflected by the first parallel light filter 13b, but the incident angle of the light becomes smaller than 45 degrees when the light is incident to the second parallel light filter 13c. Accordingly, this light is not reflected by the second parallel light filter 13c, but passes through the hollow space of the second parallel light filter 13c.

Because the parallel light filters (first parallel light filter 13b and the second parallel light filter 13c) are configured and arranged in the above-described manner, the parallel light filters 13b and 13c only filter out that component of the light incident to the parallel light filters which is not the parallel component, and only allow the parallel component of the incident light to reach the filter 13d.

The light exiting from the parallel light filters 13b and 13c and incident to the filter 13d may include not only the observation target light (e.g., fluorescence) emitted from the specimen but also other light. Specifically, the radiated light that does not contribute to the excitation of the specimen may also exit from the parallel light filter 13c and be incident to the filter 13d. This radiated light becomes a noise to the optical analysis of the specimen, and therefore it should be removed.

The filter 13d cuts off (filters out) the radiated light component from the light exiting from the parallel light filter 13c. The filter 13d may be a dielectric optical element (notch filter) embedded in the microchip 1. This is a cutting off configuration. Alternatively, the filter 13d may be a dye (pigment, colorant) embedded in the microchip 1 to absorb the radiated light component. This is an absorbing configuration.

The condensing hole 14 is defined by a cavity formed in the microchip 1. The cavity has, for example, a cylindrical shape. The light incident face of the condensing hole (cavity) 14 for the light exiting from the filter 13c reflects and condenses the incident light. Also, the light incident face of the light condensing hole 14 is configured such that the optical axis direction of the reflected and condensed light extends substantially perpendicularly to the optical axis of the incident light. In the example shown in FIG. 3, the light condensing hole 14 is configured to condense the reflected light to (at) the light introducing hole 15 for the built-in camera.

In order for the condensing hole 14 to efficiently reflect the incident light, the shape of the reflecting surface of the condensing hole 14 is decided in consideration of the critical angle of the interface (reflecting surface) that depends upon the material of the microchip 1.

Figure 7:
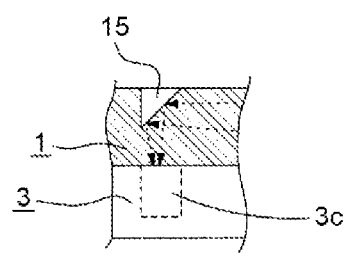
FIG. 7 shows a cross-sectional view of a light inlet hole for a built-in camera.

FIG. 7 shows the cross-sectional view of the light introducing hole 15 for the built-in camera. The bottom of the light introducing hole 15 for the built-in camera has an inclined wall. This inclined wall (inclined surface) is inclined relative to the surface of the microchip 1.

The observation target light, which is condensed by the condensing hole 14, is incident to the bottom wall of the camera light introducing hole 15. As described above, the angle of the inclined wall is appropriately decided in consideration of the critical angle and other sizes and shapes of the microchip 1, and therefore the observation target light condensed by the condensing hole 14 is turned downward (in the direction toward the built-in camera 3*c*) by the inclined wall, and condensed to the built-in camera 3*c*.

In this manner, the observation target light (e.g., fluorescence) from the specimen and the radiated light that does not contribute to the excitation of the specimen are collimated by the second lens 12*b*, the parallel light is only extracted by the two parallel light filters 13*b* and 13*c*, the parallel light is incident to the filter 13*d*, the radiated light component is cut off by the filter 13*d*, the remaining light is condensed by the condensing hole 14 and introduced to the camera light introducing hole 15, and this light is introduced to the built-in camera 3*c* of the tablet terminal device 3 by the camera light introducing hole 15. Accordingly, the observation target light is detected by the built-in camera 3*c*.

Optical Measurement and Operation/Calculation in the Tablet Terminal Device: Optical Analysis Between Steps S9 and S10 in FIG. 5, the optical analysis is carried out on the light in the fluid passage FE. The optical analysis includes the optical measurement for the solution of the specimen in the fluid passage FE, and the operation and calculation (arithmetic processing) to the measurement results.

The optical analysis is carried out in the manner, for example, as shown in FIG. 8.

Firstly, the built-in control unit 3*b* of the tablet terminal device 3 causes the display portion, which is disposed below the bottom of the light introducing hole 11, to emit light (Step S21 in FIG. 8). The light emitted from the display portion (radiated light) includes a wavelength component that is suitable for the optical measurement for the solution of the specimen present in the fluid passage FE. In other words, the radiated light includes a light component suitable for excitation of the specimen.

The light emitted from the display 3*a* and introduced to the light introducing hole 11 is condensed in the fluid passage FE via the filter 13*a* and the first lens 12*a*. Thus, the radiated light having a wavelength suitable for the excitation of the specimen is condensed to the solution of the specimen in the fluid passage FE to excite the solution of the specimen (Step S22).

The observation target light emitted from the excited specimen passes through the second lens 12*b*, the two parallel light filters 13*b* and 13*c*, the filter 13*d*, the condensing hole 14 and the camera light introducing hole 15 in this order, and is incident to the built-in camera 3*c* of the tablet terminal device 3 such that the observation target light is detected by the built-in camera 3*c* (Step S23).

A detection signal that represents the observation target light detected by the built-in camera 3*c* is sent to the built-in control unit 3*b* of the tablet terminal device 3 from the built-in camera 3*c* (Step S24).

Upon receiving the detection signal from the built-in camera 3*c*, the control unit 3*b* uses the software for analysis, which is stored in the tablet terminal device 3 beforehand or downloaded from outside via the communication function of the tablet terminal device 3, to carry out the operation and calculation (arithmetic processing) to the detection signal (Step S25).

The control unit 3*b* causes the display unit 3*a* to display the results of the processing and the results of the operation and calculation in the analysis result display area of the display unit 3*a* of the tablet terminal device 3 (Step S26).

As described above, the microchip 1 is arranged on the display unit 3*a* of the tablet terminal device 3, and the optical analysis is performed in the above-described manner. The observation target light from the specimen is detected by the built-in camera 3*c*, and the information obtained upon the detection is operated and calculated by the built-in control unit 3*b* of the tablet terminal device 3. The analysis result obtained upon the operation and the calculation is displayed in the display unit 3*a* as desired in an appropriate manner.

Modification to First Embodiment

Figure 10A:
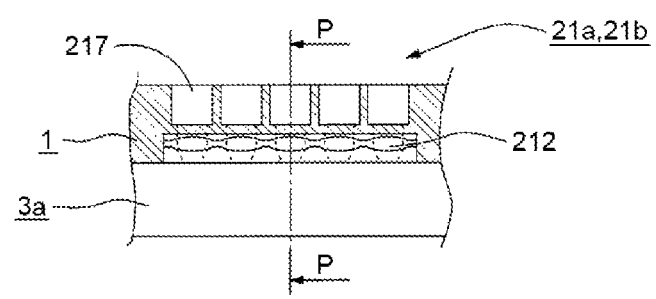
FIG. 10(a) and FIG. 10(b) show in combination the exemplary structure of the light collecting portion shown in FIG. 9. Specifically.
Figure 10B:
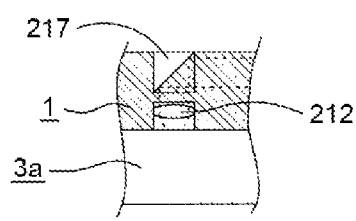

FIGS. 9 and 10 show another configuration of the light collecting unit. As shown in FIGS. 9 and 10, the light collecting unit has, for example, a liquid crystal light collimator microlens array (hereinafter, occasionally referred to as "collimator lens array 212) for collimating the light emitted from the display unit 3*a*, which has the liquid crystal panel, optical path changing holes 217 for turning the light, which exits from the collimator lens array 212, to change the optical path of the light such that the light proceeds in the microchip 1, and a condensing lens 218.

As illustrated in FIG. 10(*a*), the number of optical path changing holes 217 formed at the light exit of the collimator lens array 212 corresponds to the number of the microlenses of the collimator lens array 212.

FIG. 10(*b*) shows a cross-sectional view taken along the line P-P in FIG. 10(*a*). FIG. 10(*b*) illustrates the cross-sectional view of each optical path changing hole 217. The bottom of the optical path changing hole 217 has an inclined surface, which inclines relative to the surface of the microchip 1. The light emitted from that area of the display unit 3*a* of the tablet terminal device 3, which is present under the bottom of the optical path changing hole 217, is incident to the bottom of the optical path changing hole 217. As described above, when the microchip 1 is made from the silicone resin, and the light emitted from the microchip is incident to the inclined bottom of the optical path changing hole 217 at an incident angle that is equal to or greater than the critical angle of the microchip 1 (silicone resin) to the air, then the light is totally reflected by the inclined bottom. By appropriately deciding the angle of the inclined surface, the light emitted upward from the display unit 3*a* is reflected (turned) into a transverse direction (lateral direction) by the inclined surface, and guided such that the light proceeds in the microchip 1.

The condensing lens 218 is defined by a hollow space formed in the microchip 1. The light incident surface of the condensing lens to receive the light from the light path changing hole 217 is concave, and the light exiting surface of the condensing lens is also concave. The concave shape of the light incident surface and the concave shape of the light exiting surface are decided such that the light passing through the condensing lens 218 is condensed (collected) to the gas generation chamber of the light-driven air pumps 23 disposed at the port A and the port B.

It should be noted that in the above-described configuration, the gas generation chamber, which is located at (by) the side of the light-driven air pump 23, is irradiated with the light that exits from the optical path changing holes. If the light that exits from the optical path changing holes is collected from the upper portion of the gas generation chamber, then the ports A and B may be designed to be similar to, for example, the built-in camera light introducing hole such that the proceeding direction of the light, which passes through the condensing lens 218, may be turned to a certain extent.

The analyzing device of the above-described embodiment uses the portable tablet terminal device 3 that has the operating and calculating function, as the analyzing unit (analyzer). The analyzing device of the above-described embodiment is configured to use the microreactor, which includes the microchip 1 placed on the display unit 3a, to perform the isolation, separation, synthesis, extraction, analysis and the like for a trace amount of specimen (reagent).

Because the tablet terminal device 3 is utilized, the light emitted from the display unit 3a of the tablet terminal device 3 can be used as the light for the detection of the analysis target and as the energy for the driving. In addition, the operating and calculating unit built in the tablet terminal device 3 can be used to operate, calculate and analyze the detection data obtained from the analysis target. It is also possible to display the analysis results on the display unit.

Figure 15A:
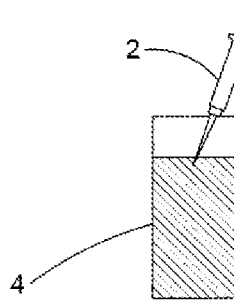
FIG. 15(a) to FIG. 15(c) show in combination a schematic process for analysis using a microchip in a conventional manner. Specifically.
Figure 15B:
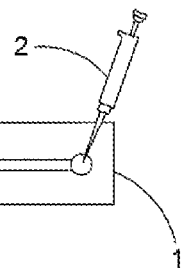
Figure 15C:
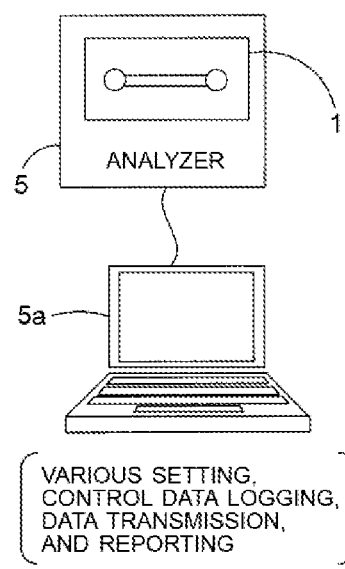

In the analyzing device of this embodiment, therefore, the light source for detection and the operating and calculating unit are integrated in the portable tablet terminal device 3. The analyzing device of this embodiment can perform the analysis with the tablet terminal device 3 and the microchip 71 that does not include active components. Unlike the conventional analyzing device, the analyzing device of this embodiment does not need a dedicated control tool (see FIG. 15). Thus, the analyzing device of this embodiment is small in size and possible to carry. The analyzing device of the above-described embodiment can conduct the testing (measurement and analysis) in a short time at a location where the analysis should be carried out, and can also provide the precise evaluation and analysis results. Consequently, the analyzing device of this embodiment meets the demand for, for example, the POCT (point of care testing) in the life science field.

The analyzing system itself is included in the tablet terminal device 3. Thus, the microchip 1 can be an inexpensive and ordinary microchip which does not include active components. Such microchip can be used as a disposal component. Accordingly, it is not necessary to use an expensive microchip that is integrated with a detection system having, for example, organic EL elements integrated therein.

The analyzing device obtains the light source and the energy source from the display liquid crystal. Thus, even if the position of the microchip 1 on the tablet terminal device 3 changes to a certain extent, the analyzing device can automatically adjust the light emitting position in accordance with the changed position. Accordingly, the position adjustment of the microchip 1 on the tablet terminal device 3 is not necessary, and the measurement can be performed quickly.

As described above, the analyzing device of this embodiment uses the communication function of the tablet terminal device 3, if necessary, to download the software for the analysis, depending upon the details of the analysis to be performed on the measurement target. Thus, the analyzing device of this embodiment can be employed as an analyzing device that can cope with a variety of analyses for a variety of specimens.

Unlike the conventional technology that prepares a dedicated detection system for a particular analysis, the single analyzing device of this embodiment can deal with various types of analyses. Thus, it is not necessary to prepare many analyzing devices that are customized for the respective analyses.

The analyzing device of this embodiment can easily perform the logging of the measured data into the tablet terminal device 3. Thus, the analyzing device of this embodiment does not need a dedicated storage unit. Also, it is easy to build up the analyzing system that uses the communication function. The displaying manner of the display unit may be customized depending upon the selection of emitted light color and the indication (displaying) of the analysis data.

It should be noted that the processing device used in the present invention is not limited to the tablet terminal device (tablet computer). In short, any suitable processing device may be employed in the analyzing device as long as the processing device has a display unit (or display portion) and possesses an operating and calculating function. For example, a personal computer, a portable telephone, a smartphone may be employed as the processing device.

Second Embodiment

Figure 11:
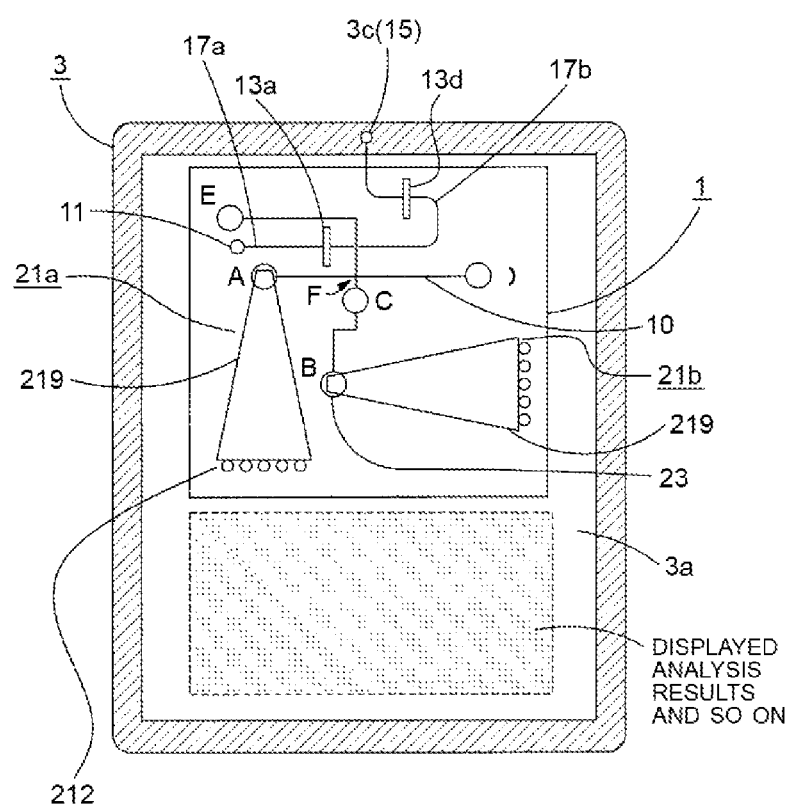
FIG. 11 shows a second embodiment of the present invention.

FIG. 11 shows a second embodiment of the present invention. The analyzing device of this embodiment is similar to the analyzing device of the first embodiment, except for the light collecting units for guiding the light from the display unit 3a of the tablet terminal device 3 to the ports A and B, and the optical analyzing unit for carrying out the optical analysis at the fluid passage 10 between the point F and the point E. The light-driven air pumps 23 are disposed in the ports A and B.

In the following description, therefore, the light collecting units and the optical analyzing unit will only be described. It should also be noted that for the sake of easier understanding, the size of the microchip 1 is exaggerated in the drawing. Thus, the actual size relationship between the tablet terminal device 3 and the microchip 1 may be different from what is depicted in FIG. 11.

Light Collecting Unit

Similar to the light collecting unit of the first embodiment, the light collecting unit of the second embodiment, which is depicted in FIG. 11, is configured to guide the light emitted from the display unit 3a of the tablet terminal device 3 to the ports A and B, which are equipped with the light-driven air pumps 23 (light-driven micropumps).

The light collecting unit has a liquid crystal light collimator microlens array 212 (collimator lens array) for collimating the light emitted from the display unit (liquid crystal panel) 3a of the light collecting unit described in the modification to the first embodiment (FIGS. 9 and 10), and also has an optical path changing holes 217 for turning the light coming from the collimator lens array 212 to change the optical path of the light such that the light proceeds in the microchip 1. A flat surface tapered light guiding path 219 is provided instead of the condensing lens 218 in the modification to the first embodiment.

The collimator lens array 212 and the optical path changing holes 217 are the same as those shown in FIG. 10. Specifically, the light emitted from the display unit 3a is collimated by the collimator lens array 212 and incident to the optical path changing holes 217.

The number of optical path changing holes 217 formed at the light exits of the collimator lenses corresponds to the number of the microlenses of the collimator lens array 212.

The light exits from the collimator lenses and is incident to the bottom of each optical path changing hole 217, which defines the inclined surface relative to the surface of the microchip 1, such that the light is turned in a lateral direction by the inclined surface having an appropriate inclination angle, which is decided in consideration of the critical angle of the material of the microchip 1 and other factors. Then, the light is incident to the flat surface tapered light guiding path 219.

The flat surface tapered light guiding path 219 has a trapezoid flat plate shape, which is elongated in the lateral direction (right-left direction in FIG. 11), when its light incident plane is compared to its light exit plane. The flat surface tapered light guiding path 219 is embedded in the microchip 1. The flat surface tapered light guiding path 219 is made from a material such as silicone resin. The material of the flat surface tapered light guiding path 219 is selected (decided) such that the refractive index of the flat surface tapered light guiding path 219 is greater than the refractive index of the material (e.g., silicone resin) of the microchip 1 and the refractive index of the air, and such that the light emitted from the display unit 3a can pass through the light guiding path 219 (the light guiding path 219 permeates the light from the display unit 3a).

The light emitted from the display unit 3a and incident to the light inlet surface of the flat surface tapered light guiding path 219 proceeds to the light exit plane while the light is spreading vertically and horizontally. Thus, part of the light from the display unit 3a is incident to the upper and lower walls and the right and left side walls of the flat surface tapered light guiding path 219 before the light reaches the light exit plane. Because the refractive index of the flat surface tapered light guiding path 219 is greater than the refractive index of the microchip 1 and the refractive index of the air, the light incident to the upper and lower walls and the right and left walls of the flat surface tapered light guiding path 219 is totally reflected and proceeds to the light exit plane if the incident angle of the light incident to the upper and lower walls and the right and left walls of the flat surface tapered light guiding path 219 is equal to or greater than the critical angle of the flat surface tapered light guiding path 219. As such, the flat surface tapered light guiding path 219 serves as the light guiding path for the light emitted from the display unit 3a. Because the flat surface tapered light guiding path 219 has the trapezoid flat plate shape and the light inlet plane is elongated in the lateral direction as compared to the light outlet plane, the light incident to the light inlet plane is condensed to a certain extent and exits from the light outlet plane.

The position and the size of the light outlet plane of the flat surface tapered light guiding path 219 are decided such that the light exiting from the light outlet plane is condensed to the gas generation chambers of the light-driven air pumps 23 disposed at the ports A and B.

It should be noted that in the above-described configuration the gas generation chamber disposed by the side of the micropump is irradiated with the light from the display unit 3a. When the light from the display unit is collected at the upper portion of the gas generation chamber, each of the ports A and B may be designed to be similar to, for example, the camera light guiding hole 15 such that the proceeding direction of the light that passes through the condensing lens 218 is turned to a desired extent if necessary.

The Optical Analyzing Unit

As shown in FIG. 11, the optical analyzing unit to carry out the optical analysis in the fluid passage FE includes an emitted light introducing hole 11, a filter 13a, an introduced light guiding path 17a, an observation light guiding path 17b, a filter 13d and a light introducing hole 15 for the built-in camera.

The emitted light introducing hole 11 is the same as the emitted light introducing hole of the first embodiment, and its detail will not be described here. As shown in FIG. 6, the bottom of the emitted light introducing hole 11 has an inclined surface, which is inclined relative to the surface of the microchip 1. The light emitted upward from the display unit 3a is turned (reflected) laterally by the inclined surface.

The light introducing (guiding) path 17a for guiding the light emitted from the display unit 3a extends from the light introducing hole 11 to the side face (lateral portion) of the fluid passage FE. The light introducing path 17a is made from a material such as silicone resin. The material of the light introducing path 17a may be decided such that the refractive index of the material is greater than the refractive index of the material (e.g., silicone resin) of the microchip 1 and the refractive index of the air, and such that the light emitted from the display unit 3a can pass through the light introducing path 17a (the light introducing path 17a permeates the light from the display unit 3a).

The light incident plane or face of the light introducing path 17a is located at a position to receive the light, which is emitted from the display unit 3a and turned by the emitted light introducing hole 11. The light exit face of the light introducing path 17a is located at a position to face the lateral portion of the fluid passage FE that is filled with the solution of the specimen diluted by the buffer solution (e.g., PBS).

The light incident to the light introducing path 17a from the light introducing hole 11 is diffused light. Therefore, part of the light is incident to the upper and lower walls (top and bottom walls) and the right and left walls of the light introducing path 17a before the light reaches the exit (light emitting end face) of the light introducing path 17a. Because the refractive index of the light introducing path 17a is greater than the refractive index of the microchip 1 and greater than the refractive index of the air, that part of the light which is incident to the upper, lower, right and left walls of the light introducing path 17a is totally reflected and proceeds toward the exit of the light introducing path 17a if the incident angle of that part of the light which is incident to the upper, lower, right and left walls of the light introducing path 17a is equal to or greater than the critical angle of the light introducing path 17a.

Accordingly, the light introducing path 17a serves as a waveguide that guides the light, which is emitted from the display unit 3a, to the solution of the specimen in the fluid passage FE such that the specimen is irradiated with the light.

A filter 13a is disposed in the light introducing path 17a between the light inlet 11 and a point arriving at the lateral portion of the fluid passage FE. The filter 13a cuts off that wavelength component which does not contribute to the excitation of the specimen, from the light introduced from the light inlet 11 of the light introducing path 17a.

Thus, the light inlet 11 collects (brings in) the light emitted from the display unit 3a, and reflects the light toward the light incident face of the light introducing path 17a. The light incident to the light introducing path 17a is introduced to the lateral portion of the fluid passage FE via the filter 13a, and the solution of the specimen diluted by the buffer solution (PBS) in the fluid passage FE is excited by the light.

The excited specimen emits light (e.g., fluorescence) depending upon the physical property of the specimen. The emitted light is used as the observation target light. The emitted light is guided by the light guiding path 17b such that the light passes through the filter 13d and the built-in camera light introducing hole 15 in this order and is incident to the built-in camera 3c of the tablet terminal device 3a. Then, the light is detected by the built-in camera 3c.

A filter 13d is disposed in the observation target light guiding path 17b between the lateral portion of the fluid passage FE and the built-in camera light introducing hole 15.

The light incident to the light incident face of the observation light guiding path 17b may include not only the observation target light (e.g., fluorescence) emitted from the specimen but also other light. Part of the light emitted from the display unit, which does not contribute to the excitation of the specimen, may proceed across the fluid passage FE and be incident to the light incident face (inlet) of the light guiding path 17b. Such light becomes a noise to the optical analysis of the specimen, and should be removed.

The filter 13d cuts off the excitation light. For example, the filter 13d may include a dielectric optical element (notch filter) or a color glass filter (absorption filter).

The built-in camera light introducing hole 15 in this embodiment is the same as the built-in camera light introducing hole of the first embodiment so that the detail of the light introducing hole 15 is omitted. As shown in FIG. 7, the bottom of the camera light introducing hole 15 has the inclined surface that is inclined relative to the surface of the microchip 1. By appropriately deciding (setting) the angle of the inclined surface in consideration of the critical angle of the microchip 1 and other factors, the observation target light introduced from the light guiding path 17b is turned downward by the inclined surface (toward the built-in camera) and condensed.

Third Embodiment

The tablet terminal device 3 that is used in the analyzing device of the above-described first and second embodiments has the camera which is built in the tablet terminal device 3. The built-in camera detects the measurement target light, and the control unit 3b that is also built in the tablet terminal device 3 operates and calculates the detected data and information.

On the other hand, the tablet terminal device 3 used in the analyzing device of the third embodiment does not have a built-in camera. The observation target light from the specimen is observed by human eyes.

Figure 12:
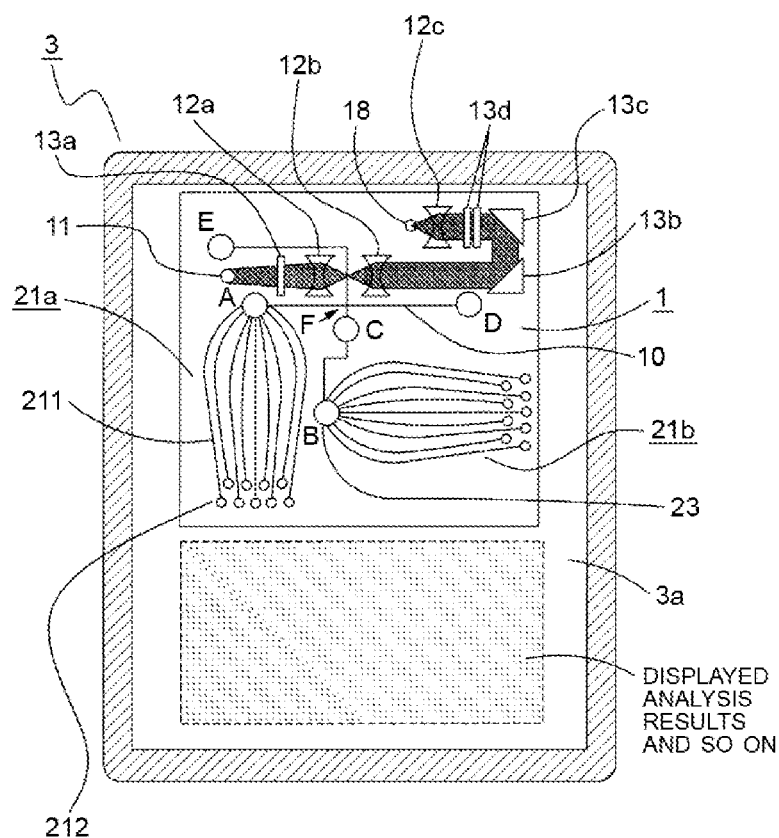
FIG. 12 shows an exemplary configuration that enables visual observation of the observation target light from the specimen in the first embodiment.

FIG. 12 illustrates an optical analyzing device that is similar to the optical analyzing device of the first embodiment shown in FIG. 3. The optical analyzing device of FIG. 12 is different from the optical analyzing device of the first embodiment in that the optical analyzing device of FIG. 12 does not have the built-in camera 3c, the camera light introducing hole 15, and the condensing hole 14, but it has a third lens 12c and an observation hole 18.

Figure 13:
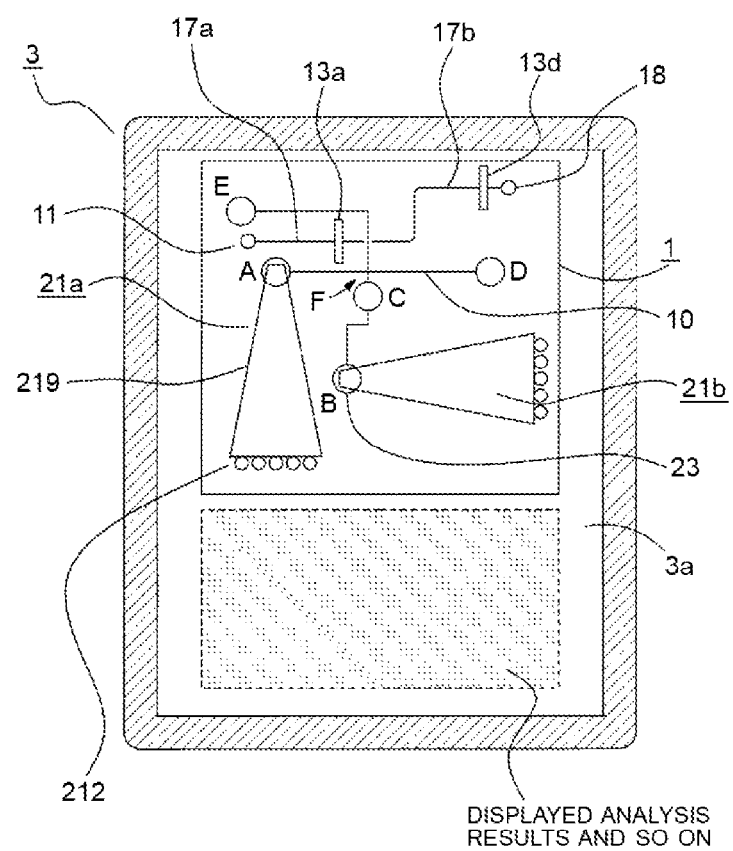
FIG. 13 shows an exemplary configuration that enables visual observation of the observation target light from the specimen in the second embodiment.

The optical analyzing device of FIG. 13 is different from the optical analyzing device of the second embodiment shown in FIG. 11 in that the optical analyzing device of FIG. 13 does not have the built-in camera and the camera light introducing hole 15, but it has an observation hole 18.

In FIG. 12, the light analyzing unit used to carry out the optical analysis on the light in the fluid passage FE includes the radiated light introducing hole 11, the first lens 12a, the second lens 12b, the two parallel light filters (first parallel light filter 13b and the second parallel light filter 13c), the filter 13d, the third lens 12c and the observation hole 18.

The structures and roles of the first lens 12a, second lens 12b, two parallel light filters (first parallel light filter 13b and second parallel light filter 13c), and filter 13d are the same as those in the first embodiment. Thus, the details of the first lens 12a, second lens 12b, two parallel light filters 13b and 13c, and filter 13d are not described here.

The third lens 12c is defined by a hollow space formed in the microchip 1. The light incident surface of the third lens 12c is concave, and the light exiting surface of the third lens 12c is also concave. The concave shape of the light incident surface and the concave shape of the light exiting surface are decided such that the light passing through the third lens 12c is incident to the observation hole 18 and condensed in the observation hole 18.

A dye (pigment, colorant) may be embedded in the observation hole 18 such that the dye may emit light when the dye is irradiated with the observation target light having a predetermined wavelength. Thus, the analysis result can be confirmed (recognized) by visual inspection (by human eyes).

In FIG. 13, on the other hand, the optical analyzing unit to carry out the optical analysis in the fluid passage FE includes a radiated light introducing hole 11, the filter 13a, the light introducing path 17a, the observation target light guiding path 17b, the filter 13d and the observation hole 18. The structures and roles of the excitation light introducing hole 11, the filter 13a, the light introducing path 17a, the observation target light guiding path 17b and the filter 13d are the same as those in the second embodiment. Thus, the details of these elements will not be described here.

The observation target light is introduced to the observation hole 18 from the light guiding path 17b. As described above, the dye (pigment, colorant) or the like is embedded in the observation hole 18 such that the dye or the like may emit light when, for example, the dye is irradiated with the observation target light having a predetermined wavelength. Thus, the analysis result of the specimen can be confirmed (recognized) by visual inspection (by human eyes).

The analyzing device of the third embodiment may be used in the optical analysis with the analysis result being recognized by human eyes. Because the analyzing device of the third embodiment does not need a built-in camera, the analyzing device of the third embodiment can be manufactured with less cost than the analyzing devices of the first and second embodiments.

Although the single microchip possesses various functions in the first, second and third embodiments, the present invention is not limited to such configurations. For example, a microchip having an optical analyzing unit may be prepared, another microchip having the light collecting unit and the light-driven air pump(s) may be prepared, and other microchip(s) may be prepared. Then, these microchips may be laminated or arranged next to each other to configure a set of microchips that serves in combination as the single microchip of the first, second or third embodiment.

Modifications to the First, Second and Third Embodiments

The microchip of any of the first to third embodiments may include a pretreatment module that has a filtering function and/or other function(s). The pretreatment module may be integrated in the microchip. The pretreatment module may include a filter for separation (e.g., for separating a blood cell and blood plasma) that has a pillar structure. Another pretreatment module may include a filter for capturing and separating a solid matter or particle. Such filters are disclosed, for example, in Patent Literatures 4, 5 and 6. The pretreatment module may separate substances which are not the specimen (e.g., blood cells, blood plasma, solid matters that are not objects to be irradiated with light, and particles that are not objects to be irradiated with light), from the specimen-containing fluid, so that the substances that are not objects to be irradiated with the light are excluded from the specimen-containing fluid.

FIGS. 14(a) and 14(b) show the pretreatment filter incorporated in the microchip of the first embodiment. FIG. 14(a) illustrates the optical analyzing device that has the pretreatment filter 30 between the port B and the intersection F to the micro fluid passage 10. The pretreatment filter 30 has a pillar structure as shown in FIG. 14(b), and is configured to separate the blood cells and/or blood plasma. The pretreatment filter 30 can perform the pretreatment such as separating the blood cells, blood plasma and the like from the liquid sent to the intersection F from the port B.

FIG. 14(a) shows the modification to the first embodiment, in which the analyzing device of the first embodiment additionally includes the pretreatment filter. It should be noted that the second embodiment or the third embodiment may also include the pretreatment filter.

In FIG. 14, the pretreatment filter is incorporated in the microchip 1. Alternatively, a chip that has the same function as the pretreatment filter may be prepared beforehand, and this chip may be laminated on the microchip of the first embodiment (or any other suitable embodiment) with a fluid passage being connected to impart the pretreatment function to the microchip, or this chip may be arranged next to the microchip with a fluid passage being connected to impart the pretreatment function to the microchip.

REFERENCE NUMERALS AND SIGNS

1: Microchip
2: Micropipette
3: Tablet device (processing device)
3a: Display unit
3b: Control unit
3c: Built-in camera
4: Specimen
10: Micro fluid passage
11: Radiated light introducing hole
12a: First lens
12b: Second lens
12c: Third lens
13a, 13d: Filter
13b, 13c: First parallel light filter, and second parallel light filter
14: Condensing hole
15: Light introducing hole for a built-in camera
17a: Light guiding path
17b: Observation target light guiding path
18: Observation hole
21a, 21b: Light collecting unit
23: Light-driven air pump
211: Optical fiber
212: Liquid crystal light collimating microlens array
213: Liquid crystal light condensing microlens array
214: Optical fiber manifold
215: Light condensing hole
216: Light introducing hole
217: Optical path changing hole
218: Light condensing lens
219: Flat tapered light-guiding path
30: Pretreatment filter
A-E: Ports

The invention claimed is:

1. An optical analyzing device comprising:
a processing device that includes a display unit for displaying an image, and a built-in control unit for carrying out operation and calculation and controlling the image to be displayed on the display unit; and
a microchip having a passage to which a liquid containing a specimen is introduced, a light inlet through which a radiation light is introduced into the microchip, a hole for receiving a driving light, a light-driven liquid conveying unit driven by the driving light for conveying the liquid in the passage, and a light outlet from which an emission light emitted by the specimen exits, the passage having a light radiation position at which the liquid is irradiated by the radiation light,
the control unit of the processing device being configured to cause the display unit to emit the radiation light for introducing the radiation light into the light inlet from the display unit and for irradiating the liquid at the light radiation position in the passage with the radiation light to cause the specimen contained in the liquid to emit the emission light the control unit being configured to cause the display unit to emit the driving light for introducing the driving light into the hole for driving the light-driven liquid conveying unit to convey the liquid to the light radiation position.

2. The optical analyzing device according to claim 1, wherein the microchip includes a light collecting unit, and the light collecting unit has a light collecting portion for collecting the driving light introduced from the hole, and a light guiding unit for guiding the driving light collected by the collecting portion to the light-driven liquid conveying unit.

3. The optical analyzing device according to claim 2, wherein the processing device includes an image receiving unit, the light outlet of the microchip is placed at a position that allows the image receiving unit to receive the emission light exiting from the light outlet, and the control unit carries out the operation and calculation based on a signal representing the emission light, which exits from the light outlet and is received by the image receiving unit, to analyze the specimen.

4. The optical analyzing device according to claim 2, wherein the light outlet of the microchip is placed at a position that allows the emission light, which exits from the light outlet, to be observed by a human eye.

5. The optical analyzing device according to claim 2, wherein the microchip is configured to take a wavelength component that is necessary for excitation of the specimen from the radiation light introduced from the light inlet, and irradiate the liquid, which contains the specimen introduced to the microchip, with the wavelength component to cause the liquid, which contains the specimen, to emit the emission light,
the microchip includes a passive element configured to cut off the wavelength component from the emission light emitted from the liquid, which contains the specimen, such that emission light from the passive element is guided to the light outlet.

6. The optical analyzing device according to claim 2, wherein the microchip includes a pretreatment filter configured to separate a substance, which is not the specimen, from the liquid, which contains the specimen, before the liquid, which contains the specimen, is irradiated with the light.

7. The optical analyzing device according to claim 1, wherein the processing device includes an image receiving unit, the light outlet of the microchip is placed at a position that allows the image receiving unit to receive the emission light exiting from the light outlet, and the control unit carries out the operation and calculation based on a signal representing the emission light, which exits from the light outlet and is received by the image receiving unit, to analyze the specimen.

8. The optical analyzing device according to claim 7, wherein the microchip is configured to take a wavelength component that is necessary for excitation of the specimen from the radiation light introduced from the light inlet, and irradiate the liquid, which contains the specimen introduced to the microchip, with the wavelength component to cause the liquid which contains the specimen, to emit the emission light,
the microchip includes a passive element configured to cut off the wavelength component from the emission light emitted from the liquid, which contains the specimen, such that emission light from the passive element is guided to the light outlet.

9. The optical analyzing device according to claim 7, wherein the microchip includes a pretreatment filter configured to separate a substance, which is not the specimen, from the liquid, which contains the specimen, before the liquid, which contains the specimen, is irradiated with the radiation light.

10. The optical analyzing device according to claim 7, wherein the image receiving unit includes a built-in camera.

11. The optical analyzing device according to claim 1, wherein the light outlet of the microchip is placed at a position that allows the emission light, which exits from the light outlet, to be observed by a human eye.

12. The optical analyzing device according to claim 11, wherein the microchip is configured to take a wavelength component that is necessary for excitation of the specimen from the radiation light introduced from the light inlet to, and irradiate the liquid, which contains the specimen introduced to the microchip, with the wavelength component to cause the liquid, which contains the specimen, to emit the emission light,
the microchip includes a passive element configured to cut off the wavelength component from the emission light emitted from the liquid, which contains the specimen, such that the emission light from the passive element is guided to the light outlet.

13. The optical analyzing device according to claim 11, wherein the microchip includes a pretreatment filter configured to separate a substance, which is not the specimen, from the liquid, which contains the specimen, before the liquid, which contains the specimen, is irradiated with the radiation light.

14. The optical analyzing device according to claim 1, wherein the microchip is configured to take a wavelength component that is necessary for excitation of the specimen from the radiation light introduced from the light inlet, and irradiate the liquid, which contains the specimen introduced to the microchip, with the wavelength component to cause the liquid, which contains the specimen, to emit the emission light,
the microchip includes a passive element configured to cut off the wavelength component from the emission light emitted from the liquid, which contains the specimen, such that emission light from the passive element is guided to the light outlet.

15. The optical analyzing device according to claim 14, wherein the microchip includes a pretreatment filter configured to separate a substance, which is not the specimen, from the liquid, which contains the specimen, before the liquid, which contains the specimen, is irradiated with the radiation light.

16. The optical analyzing device according to claim 1, wherein the microchip includes a pretreatment filter configured to separate a substance, which is not the specimen, from the liquid, which contains the specimen, before the liquid, which contains the specimen, is irradiated with the radiation light.

17. The optical analyzing device according to claim 1, wherein the processing device is a portable tablet device.

18. The optical analyzing device according to claim 1, wherein the microchip further having a reservoir for reserving the specimen, a further hole for receiving a further driving light, and a further light-driven liquid conveying unit driven by the further driving light for conveying the specimen reserved in the reservoir to the passage for mixing the specimen with the liquid,
wherein the control unit is configured to cause the display unit to emit the further driving light for introducing the further driving light into the further hole for driving the further light-driven liquid conveying unit to mix the specimen with the liquid before conveying the liquid with the specimen to the light radiation position.

19. An optical analyzing method for analyzing a specimen with the use of the optical analyzing device according to claim 18, comprising:
preparing the processing device;
placing the microchip on the display unit of the processing device;
causing the display unit for introducing the further driving light into the further hole for driving the further light-driven liquid conveying unit to mix the specimen with the liquid;
causing the display unit for introducing the driving light into the hole of the microchip for driving the light-driven liquid conveying unit to convey the liquid with the specimen to the light radiation position in the passage of the microchip; and
causing the display unit for introducing the radiation light into the light inlet of the microchip for irradiating the liquid at the light radiation position with the radiation light to cause the specimen contained in the liquid to emit the emission light for analyzing the specimen with the use of the emission light.

20. An optical analyzing method for analyzing a specimen with the use of the optical analyzing device according to claim 1, comprising:
preparing the processing device;
placing the microchip on the display unit of the processing device;
causing the display unit for introducing the driving light into the hole of the microchip for driving the light-driven liquid conveying unit to convey the liquid to the light radiation position in the passage of the microchip; and
causing the display unit for introducing the radiation light into the light inlet of the microchip for irradiating the liquid at the light radiation position with the radiation light to cause the specimen contained in the liquid to emit the emission light for analyzing the specimen with the use of the emission light.

21. A microchip configured to be placed on a display unit of a processing device, and optically analyze a specimen introduced to the microchip upon light emission of the display unit, the processing device having the display unit for displaying an image, the microchip comprising:
- a passage to which a liquid containing a specimen is introduced;
- a light inlet being configured to receive a radiation light emitted by the display unit of the processing device, the passage having a light radiation position at which the liquid is irradiated by the radiation light and the specimen contained in the liquid emits an emission light;
- a hole for receiving a driving light emitted by the display unit of the processing device;
- a light-driven liquid conveying unit driven by the driving light for conveying the liquid in the passage to the light radiation position; and
- a light outlet from which the emission light emitted by the specimen exits,
- the light outlet being configured to guide the emission light emitted from the liquid to outside.

22. The microchip according to claim 21, further comprising:
- a reservoir for reserving the specimen;
- a further hole for receiving a further driving light emitted by the display unit of the processing device; and
- a further light-driven liquid conveying unit driven by the further driving light for conveying the specimen reserved in the reservoir to the passage for mixing the specimen with the liquid before the liquid containing the specimen is conveyed to the light radiation position.

23. A processing device for optical analysis comprising:
- a display unit configured to display an image; and
- a built-in control unit configured to carry out operation and calculation and to control the image to be displayed on the display unit;
- the processing device being configured to introduce light to a microchip from the display unit to analyze a specimen introduced to the microchip, the microchip having a light inlet, a passage to which a liquid containing the specimen is introduced, a hole, a light-driven liquid conveying unit for conveying the liquid in the passage, and a light outlet and being placed on the display unit,
- the control unit of the processing device being configured to cause the display unit for introducing a driving light into the hole of the microchip for driving the light-driven liquid conveying unit to convey the liquid to a light radiation position in the passage of the microchip, and to cause the display unit for introducing a radiation light into the light inlet of the microchip for irradiating the liquid at the light radiation position with the light to cause the specimen contained in the liquid to emit an emission light for analyzing the specimen with the use of the emission light.

24. The processing device according to claim 23, wherein the control unit of the processing device is configured to cause the display unit for introducing a further driving light into a further hole of the microchip for driving a further light-driven liquid conveying unit in the microchip for mixing the specimen with the liquid before the liquid containing the specimen is conveyed to the light radiation position.

25. An optical analyzing device comprising:
- a processing device that includes a display unit for displaying an image, and a built-in control unit for carrying out operation and calculation and controlling the image to be displayed on the display unit; and
- a microchip having a passage to which a liquid containing a specimen is introduced, a light inlet through which a radiation light is introduced into the microchip, and a light outlet from which an emission light emitted by the specimen exits, the passage having a light radiation position at which the liquid is irradiated by the radiation light, the light inlet having a bottom wall inclined with respect to the light inlet, so that the radiation light is reflected in a lateral direction of the microchip by the bottom wall and guided to the light radiation position,
- the control unit of the processing device being configured to cause the display unit to emit the radiation light for introducing the radiation light into the light inlet from the display unit and for irradiating the liquid at the light radiation position in the passage with the radiation light to cause the specimen contained in the liquid to emit the emission light.

26. An optical analyzing method for analyzing a specimen with the use of the optical analyzing device according to claim 25, comprising:
- preparing the processing device;
- placing the microchip on the display unit of the processing device;
- conveying the liquid to the light radiation position in the passage of the microchip; and
- causing the display unit for introducing the radiation light into the light inlet of the microchip for irradiating the liquid at the light radiation position with the radiation light to cause the specimen contained in the liquid to emit the emission light for analyzing the specimen with the use of the emission light.

27. The optical analyzing method according to claim 26, further comprising
condensing the radiation light reflected by the bottom wall before irradiating the liquid at the light radiation position.

28. The optical analyzing method according to claim 27, further comprising
collimating the emission light before the emission light reaches the light outlet.

29. The optical analyzing method according to claim 28, further comprising
condensing the collimated emission light before the emission light reaches the light outlet.

30. A microchip configured to be placed on a display unit of a processing device, and optically analyze a specimen introduced to the microchip upon light emission of the display unit, the processing device having the display unit for displaying an image, the microchip comprising:
- a passage to which a liquid containing a specimen is introduced;
- a light inlet being configured to receive a radiation light emitted by the display unit of the processing device, the passage having a light radiation position at which the liquid is irradiated by the radiation light and the specimen contained in the liquid emits an emission light; and
- a light outlet from which the emission light emitted by the specimen exits, the light inlet having a bottom wall inclined with respect to the light inlet, so that the radiation light is reflected in a lateral direction of the microchip by the bottom wall and guided to the light radiation position.

31. The microchip according to claim 30, further comprising a first lens configured to condense the radiation light reflected by the bottom wall before irradiating the liquid at the light radiation position.

32. The microchip according to claim 31, further comprising a second lens configured to collimate the emission light before the emission light reaches the light outlet.

33. The microchip according to claim 32, further comprising a condensing hole configured to condense the emission light collimated by the second lens before the emission light reaches the light outlet.

* * * * *